US008071796B2

(12) United States Patent
Schweizer et al.

(10) Patent No.: US 8,071,796 B2
(45) Date of Patent: Dec. 6, 2011

(54) PROCESS FOR THE MANUFACTURE OF NON-STEROIDAL ANTI-INFLAMMATORY AGENTS AND INTERMEDIATES THEREOF

(75) Inventors: Steffen Schweizer, Berlin (DE); Alfred Olbrich, Halle/Westf. (DE)

(73) Assignee: Intendis GmbH, Berlin (DE)

( * ) Notice: Subject to any disclaimer, the term of this patent is extended or adjusted under 35 U.S.C. 154(b) by 0 days.

(21) Appl. No.: 12/104,772

(22) Filed: Apr. 17, 2008

(65) Prior Publication Data

US 2008/0274517 A1 Nov. 6, 2008

Related U.S. Application Data

(60) Provisional application No. 60/912,596, filed on Apr. 18, 2007.

(30) Foreign Application Priority Data

Apr. 18, 2007 (EP) ..................................... 07090075
May 3, 2007 (EP) ..................................... 07008931

(51) Int. Cl.
*C07D 307/87* (2006.01)
*C07D 401/02* (2006.01)
(52) U.S. Cl. ....................... 549/462; 546/167
(58) Field of Classification Search .................. 546/167; 549/562
See application file for complete search history.

(56) References Cited

U.S. PATENT DOCUMENTS
7,417,056 B2 * 8/2008 Jaroch et al. .................. 514/310

FOREIGN PATENT DOCUMENTS
WO WO 2006050998 A1 * 5/2006

OTHER PUBLICATIONS

Wikipedia enzymatic resolution , 2010.*
Reetz M., Current Opinion in Chemical Biology, vol. 6, issue 2, 2002, p. 145-150.*
Google search under enzymatic resolution.*
Krimmel et al. Organic Synthesis, Coll. vol. 4, p. 960 (1963).*

* cited by examiner

*Primary Examiner* — Yong Chu
(74) *Attorney, Agent, or Firm* — Millen, White, Zelano, Branigan, P.C.

(57) ABSTRACT

The current invention describes novel chiral synthetic routes and intermediates for the manufacture of chiral anti-inflammatory agents of general formula VIII

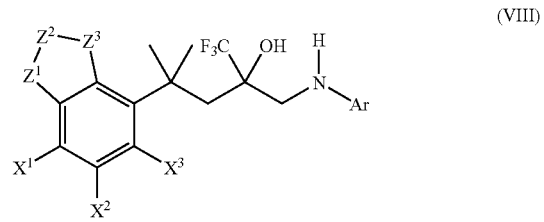

(VIII)

in which at least one of the groups $X^1$, $X^2$, $X^3$ is selected from fluoro, chloro, bromo, hydroxy, methoxy, ethoxy, trifluoromethyl, amino whereas the other groups $X^1$, $X^2$, $X^3$ have the meaning of a hydrogen atom,
in which at least one of the groups $Z^1$, $Z^2$, $Z^3$ is selected from —O—, —S—, —NH—, —N(—CH$_3$)—,
whereas the other groups $Z^1$, $Z^2$, $Z^3$ have the meaning of a —CH$_2$— group,
and in which Ar is an aromatic group.

17 Claims, No Drawings

PROCESS FOR THE MANUFACTURE OF NON-STEROIDAL ANTI-INFLAMMATORY AGENTS AND INTERMEDIATES THEREOF

This application claims the benefit of the filing date of U.S. Provisional Application Ser. No. 60/912,596 filed Apr. 18, 2007, EP 07090075.8 filed Apr. 18, 2007, and EP 07008931.3 filed May 9, 2007.

BACKGROUND OF THE INVENTION

Compounds of general formula VIII

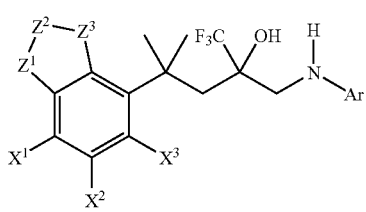

in which at least one of the groups $X^1$, $X^2$, $X^3$ is selected from fluoro, chloro, bromo, hydroxy, methoxy, ethoxy, trifluoromethyl, amino whereas the other groups $X^1$, $X^2$, $X^3$ have the meaning of a hydrogen atom,
in which at least one one of the groups $Z^1$, $Z^2$, $Z^3$ is selected from —O—, —S—, —NH—, —N(—$CH_3$)—,
whereas the other groups $Z^1$, $Z^2$, $Z^3$ have the meaning of a —$CH_2$— group,
and in which Ar is an aromatic group
are described as powerful anti-inflammatory agents (e.g. WO 98/54159, WO 00/32584, WO 02/10143, WO 03/082827, WO 03/082280, WO 2004/063163 and WO 2006/050998).

However, the processes for the manufacturing of the compounds of general formula VIII have quite a number of steps, resulting in low yields of the whole chain of reactions and are not suitable for large scale productions.

OBJECT OF THE INVENTION

It is therefore the object of the invention to make available a novel process characterized a higher total yield achieved by the same or lower number of steps which is suitable for pharmaceutical production. The object of the invention is achieved by the processes described herein.

GENERAL DESCRIPTION OF THE INVENTION AND PREFERRED EMBODIMENTS

An essential element of the synthetic route described herein is the compound of general formula I

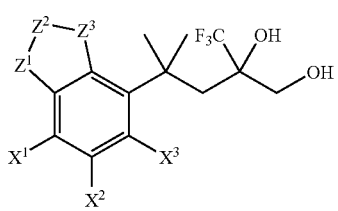

in which at least one of the groups $X^1$, $X^2$, $X^3$ is selected from fluoro, chloro, bromo, hydroxy, methoxy, ethoxy, trifluoromethyl, amino whereas the other groups $X^1$, $X^2$, $X^3$ have the meaning of a hydrogen atom,
and in which at least one of the groups $Z^1$, $Z^2$, $Z^3$ is selected from —O—, —S—, —NH—, —N(—$CH_3$)—,
whereas the other groups $Z^1$, $Z^2$, $Z^3$ have the meaning of a —$CH_2$— group.

Another aspect of the invention is a manufacturing method according to which the compounds of general formula VIII can be produced in an enantiomerically pure form (enantiomeric excess ee >>80%). It is clear to the expert in the art that the compounds of the prior art are—when used as pharmaceuticals—usually in an enantiomerically pure form. It is therefore important to develop a manufacturing route that is able to produce the compounds of general formula VIII in enantiomerically pure form. This object is also achieved by the present invention. The starting materials of the process described herein (2-hydroxy-4-methyl-2-(trifluoromethyl) pentenoic acid) may be used in the described processes in enantiomerically pure form, subsequently yielding the final compound in enantiomerically pure form.

The compound 2-hydroxy-4-methyl-2-(trifluoromethyl) pentenoic acid may be generated according to the method described by Mikami (Tetrahedron: Asymmetry 15 (2004) 3885-3889). It is also possible to use racemic alkyl 2-hydroxy-4-methyl-2-(trifluoromethyl)-pentenoate or the free acid thereof and separate the enantiomers by enzymatic hydrolysis.

It is therefore an object of the present invention to provide a process in which the desired enantiomerically pure 2-hydroxy-4-methyl-2-(trifluormethyl)pentenoic acid is separated from the undesired enantiomer by way of enzymatic hydrolysis.

Using enantiomerically pure or enriched (ee >>80%) 2-hydroxy-4-methyl-2-(trifluormethyl)pentenoic acid as the starting materials results in an enantiomerically pure compound of general formula VIII. The advantage of the described reaction starting with enantiomerically pure or enriched 2-hydroxy-4-methyl-2-(trifluormethyl)pentenoic acid is that it avoids the synthesis of an undesired enantiomer and it avoids carrying the same through following steps, therefore avoiding the separation of the enantiomers at a later stage (or even in the final product) and therefore being much more efficient.

The general method for the production of the compounds of general formula VIII via the compound of general formula I is described below in detail. The expert in the art is fully aware of the fact that a number of variants of the reaction route are possible without deviating from the general teaching of the present invention. It is for example possible to not isolate all intermediates of the synthetic route.

The process for the manufacturing starts with a compound of general formula IV

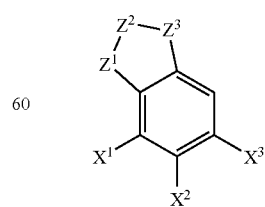

in which $X^1$, $X^2$, $X^3$, $Z^1$, $Z^2$, $Z^3$ have meaning described above.

The compound of general formula IV is reacted with 2-hydroxy-4-methyl-2-(trifluoro-methyl)pentenoic acid

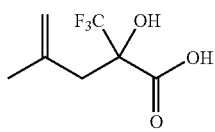

(2-hydroxy-4-methyl-2-(trifluoromethyl)pentenoic acid) to yield a compound of general formula II

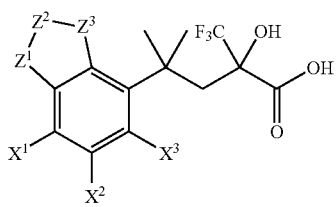

in which $X^1$, $X^2$, $X^3$, $Z^1$, $Z^2$, $Z^3$ have the above described meaning.

The reaction described above is carried out in a organic solvent in the presence of a lewis acid. Suitable solvents are e.g. polar solvents or halogenated solvents, the preferred solvents include dichloromethane and dichloroethane. The lewis acid may be aluminium chloride, $BF_3$, HF, or phosphoric acid.

In a preferred embodiment of the invention the compound according to formula IV is solved in a halogenated solvent (e.g. $CH_2Cl_2$) $AlCl_3$ is added and finally the 2-hydroxy-4-methyl-2-(trifluoromethyl)pentenoic acid is added to the stirred solution. In an even more preferred embodiment the addition of $AlCl_3$ and the 2-hydroxy-4-methyl-2-(trifluoromethyl)pentenoic acid is carried out at 0-5° C., the mixture is allowed to come to room temperature and the mixture is continued to stir for 4-120 hours at room temperature.

It is furthermore preferred that 1.5 equivalents of the compound according to formula IV are used, 2 equivalents $AlCl_3$ and 1.0 equivalent of 2-hydroxy-4-methyl-2-(trifluoromethyl)pentenoic acid.

The reaction described above can be carried out with enantiomerically pure 2-hydroxy-4-methyl-2-(trifluoromethyl)pentenoic acid. The enantiomeric pure 2-hydroxy-4-methyl-2-(trifluoromethyl)pentenoic acid may be synthesized under asymmetric catalysis as described by Mikami (see above) or the racemic form may be enzymatically hydrolized.

The asymmetric hydrolysis may be carried out in water. If necessary polar organic solvents (e.g. DMSO, lower alcohols) may be added to enhance solubility of the substrate. The reaction mixture may be buffered (phosphate or similar suitable buffers) to keep the pH of the reaction mixture at constant level as required by the individual enzyme.

Quite a number of enzymes are possible for the enzymatic hydrolysis. These include the hydrolases (EC3.hydrolases) of the subclasses EC3.1. (carboxylic esterhydrolasis in particular).

Such hydrolases are commercially available from various sources, e.g.

1. Alphamerics Limited, UK
    Lipase C1, Lipase C2, Lipase A, Lipase AS1, Lipase AN, Lipase PC, Lipase PF, Lipase B (CALB)
2. Amano Enzyme Inc., Japan
    Lipase AH, Lipase AK, Lipase AYS, Lipase PS, Protease K, Protease N, Protease P
3. Biocatalytics Incorporated., USA
    ICR-101, ICR-102, ICR-103, ICR-104, ICR-105, ICR-106, ICR-107, ICR-108, ICR-109, ICR-110, ICR-111, ICR-112, ICR-113, ICR-114, ICR-115, ICR-116, ICR-117, ICR-118, ICR-19, ICR-120, IMW-102, IMW-105
4. Julich Chiral Solutions, Germany
    Esterase BS1, Esterase BS2, Esterase BS3, Esterase PF2, Esterase PL
5. NovoNordisk/Novozyme (Denmark)
    Duramyl, Novozyme 868, Novozyme 525L, Novozyme 388, Neutrase 0, Liopoase
6. Sigma, Germany
    Lipase from porcine pancreas Typ II, Esterase porcine liver, Lipase *candida rugosa*.

The expert in the art is aware of further enzymes that may achieve the same result.

The enzymatic hydrolysis is carried out as follows: Racemic alkyl 2-hydroxy-4-methyl-2-(trifluoromethyl)pentenoate is used as starting material. The alkyl group may be a $C_1$-$C_5$ alkyl group which may be a straight chain or branched. Preferably the alkyl group is an ethyl group. It is emulsified in water, the pH is adjusted, the enzyme is added at temperature from about 10° C. to about 60° C. Temperature, pH and reaction time may vary depending on the individual enzyme. The reaction time may be up to 300 hours. The reaction conditions have to be tested under control (e.g. GC control) to find the optimum.

It is an advantageous feature of the process according to the invention that no saponification step is needed. A saponification is needed in a process in which alkyl 2-hydroxy-4-methyl-2-(trifluoromethyl)pentenoate bis reacted with a compound of formula IV yielding an alkyl ester of compound II.

It is surprising for the expert skilled in the art that the reaction of the compound of formula IV with 2-hydroxy-4-methyl-2-(trifluoromethyl)pentenoic acid in the presence of a lewis acid yields the compound of general formula II.

It is even more surprising that the reaction of the compound of formula IV with 2-hydroxy-4-methyl-2-(trifluoromethyl) pentenoic acid in the presence of a lewis acid (i.e. under Friedel-Craft conditions) is carried out up to 10 times faster and with higher yields than with alkyl esters.

The compound of general formula II may be reduced to the key compound of general formula I

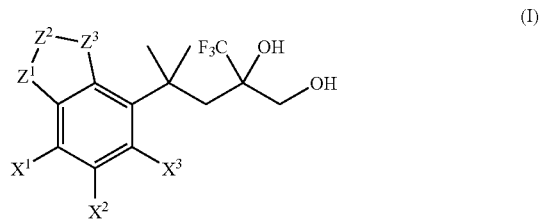

by e.g. lithium aluminium hydride or lithium borohydride.

Enantiomerically pure compounds of general formula I are key compounds of the process, and are therefore a further object of the invention. Preferred embodiments of the compounds of formula I are those which have one of the following substitution patterns:

| | $Z^1$ | $Z^2$ | $Z^3$ | $X^1$ | $X^2$ | $X^3$ | enantiomer |
|---|---|---|---|---|---|---|---|
| a) | O | | | F | | | R |
| b) | | O | | | F | | R |
| c) | | | O | | | F | R |
| d) | NH | | | F | | | R |
| e) | | | O | | F | | R |
| f) | S | | | | | F | R |
| g) | | NH | | Cl | | | R |
| h) | | | NH | | Cl | | R |
| i) | | | S | | | Cl | R |
| j) | | S | | $CF_3$ | | | R |
| k) | S | | | | $CF_3$ | | R |
| l) | O | | | | | $CF_3$ | R |
| m) | | O | | O—$CH_3$ | | | R |
| n) | | | O | | O—$CH_3$ | | R |
| o) | | O | O | | | O—$CH_3$ | R |
| p) | O | | | | F | | R |
| q) | NH | | | | | F | R |
| r) | | NH | | $NH_2$ | | | R |
| s) | | NH | | | $NH_2$ | | R |
| t) | | | O | | | Br | R |
| u) | O | | | F | | | S |
| v) | | O | | | F | | S |
| w) | | | O | | F | | S |
| x) | NH | | | F | | | S |
| y) | | | O | | F | | S |
| z) | S | | | | | F | S |
| aa) | | NH | | Cl | | | S |
| bb) | | | NH | | Cl | | S |
| cc) | | | S | | | Cl | S |
| dd) | | S | | $CF_3$ | | | S |
| ee) | S | | | | $CF_3$ | | S |
| ff) | O | | | | | $CF_3$ | S |
| gg) | | O | | O—$CH_3$ | | | S |
| hh) | | | O | | O—$CH_3$ | | S |
| ii) | | O | O | | | O—$CH_3$ | S |
| jj) | O | | | | F | | S |
| kk) | NH | | | | | F | S |
| ll) | | NH | | $NH_2$ | | | S |
| mm) | | NH | | | $NH_2$ | | S |
| nn) | | | O | | | Br | S |

Enantiomerically pure in the context of this invention means an enantiomeric excess (ee)>80%. It has to be understood that according to the present invention it is possible to synthesize compounds of ee>90%, ee>95%, ee>97% and even ee>99%.

The compound of general formula I is then oxydized to form the aldehyde of general formula V

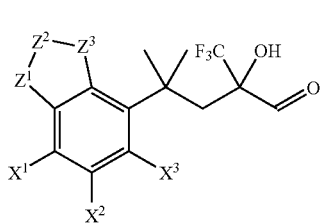

(V)

in which $X^1$, $X^2$, $X^3$, $Z^1$, $Z^2$, $Z^3$ have the meaning described above.

The oxidation may be carried out by $SO_3$/pyridin complex or with oxalylchloride/DMSO (Swern oxidation). The expert in the art is aware of other possibilities to oxydize the alcohol of formula I to the aldehyde of formula V.

The aldehyde of general formula V is then reacted with an aromatic amine of general formula VI $$H_2N—Ar \qquad (VI)$$

in which Ar is an aromatic group.

The compound according to general formula VI may be any aromatic amine. Preferred embodiments of the compounds of general formula VI are selected from the following list:

1-amino-2-methyl-benzene
1-amino-4-methyl-benzene
2-amino-4-methylpyridine
2-amino-pyridine
2-amino-pyrimidine
3-amino-quinoline
4-amino-pyridine
4-amino-pyrimidine
5-amino-isoquinoline
5-amino-1-methyl-isoquinoline
5-amino-2,6-di-methylquinoline
5-amino-2-methyl-indole
5-amino-2-methyl-isoquinol-1(2H)-one
5-amino-2-methylquinoline
5-amino-6-chloro-2-methylquinoline
5-amino-6-fluoro-2-methylquinoline
5-amino-isoquinol-2(1H)-one
5-amino-quinoline
amino-benzene
N-(4-aminophenyl)-piperidine.

The generated imine of formula VII

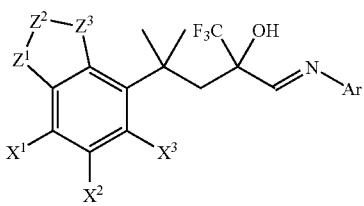

(VII)

in which $X^1$, $X^2$, $X^3$, $Z^1$, $Z^2$, $Z^3$ and Ar have the meaning described above is subsequently reduced in order to yield the compound according to general formula VIII. The reaction may be carried out by sodium borohydride in alcoholic solution (or in THF), it may also be carried out by $H_2/Ni$.

A key advantage of the present invention compared to state of the art synthesis that it avoids the purification of an alkyl ester of compound II. Such alkyl ester (which is the product of the reaction of alkyl 2-hydroxy-4-methyl-2-(trifluoromethyl)pentenoate with a compound of formula IV) needs to be separated from the starting compound IV by crystallization.

According to the present invention the necessary separation of compound IV can be made at the stage of compound II (i.e. by using free acid 2-hydroxy-4-methyl-2-(trifluoromethyl)-pentenoic acid as the starting material). At the stage of compound II the separation from compound IV can be made using acid-base-extraction (which is more efficient compared to crystallization of the alkyl ester of compound II).

As described above the expert in the art knows a number of variations and deviations from the process steps described herein. It is therefore clear that the invention described in the claims encompasses further variants and deviations which are obvious to the expert in the art or can easily be identified by the expert in the art without any need to be inventive.

The process steps described above are furthermore described in the following examples which are not meant to limit the invention in any way.

EXAMPLES

1) Synthesis of ethyl-2-hydroxy-4-methyl-2-(trifluoromethyl)pentenoate

A suspension of 0.27 mol Mn and 0.01 mol $ZnCl_2$ in 105 ml THF is heated to reflux. 0.01 mol 3-bromo-2-methyl-1-propene is added to the boiling mixture and after 30 minutes a solution of 0.11 mmol ethyl-trifluoropyruvate and 0.18 mol 2-bromo-2-methyl-1-propene in 90 ml THF is dropped to the reaction mixture within 2.5 hours. After 3 hours under reflux the mixture is stirred for 19 hours at room temperature. The reaction mixture is poured on 90 ml of a saturated $NH_4Cl$ and ice mixture. After vigorous stirring for 30 minutes the mixture is extracted four times with 110 ml of MTBE each. The combined organic extracts are washed with 30 ml of brine, dried over magnesiumsulfate and concentrated in vacuo. The residue is destined under reduced pressure. ethyl-2-hydroxy-4-methyl-2-(trifluoromethyl)pentenoate is obtained in 73% yield.

2) Synthesis of 2-hydroxy-4-methyl-2-(trifluoromethyl)pentenoic Acid

Ethyl 2-hydroxy-4-methyl-2-(trifluoromethyl)pentenoate is used as starting material. 27.1 g (120 mmole) ethyl 2-hydroxy-4-methyl-2-(trifluoromethyl)pentenoate is emulsified in 60 mL water, the pH is adjusted to 8.0 with sodium hydroxide solution, the solution is stirred at room temperature. 6 g of the enzyme (Novozyme 388) is added at room temperature. The mixture is stirred for 10 hours under GC control.

The aqueous solution is extracted two times with 100 mL of MTBE. The aqueous phase is acidified to pH 1 with HCl solution, treated with diatomaceous earth and MTBE and filtered. The aqueous is was separated and extracted three times with MTBE. The organic phase is evaporated to dryness to obtain a light brownish solid. The crude 2-hydroxy-4-methyl-2-(trifluoromethyl)pentenoic acid is crystallized from n-heptane. The yield of (R)-2-hydroxy-4-methyl-2-(trifluoromethyl)pentenoic acid is 25%.

The reaction conditions have to adapted to the individual enzyme by changing solvent, buffer, pH, temperature, reaction time in order to achieve optimum results for the desired (R)- or (S)-2-hydroxy-4-methyl-2-(trifluoromethyl)pentenoic acid.

3) Synthesis of 4-(5-fluoro-2,3-dihydro-benzofuran-7-yl)-2-hydroxy-4-methyl-2-(trifluoromethyl)pentanoic Acid A solution of 0.07 mol 5-fluoro-2,3-dihydro-benzofurane in 21 ml of dichloromethane is cooled to 3° C. To this solution 0.1 mol of $AlCl_3$ is added over a period of 30 minutes. After this addition 0.05 mol of 2-hydroxy-4-methyl-2-(trifluoromethyl)pentenoic acid is added dropwise over 30 minutes. The mixture is stirred for at least 6 h under reflux conditions. After complete reaction the solution is poured on a mixture of ice (50 ml) and 1M HCl (10 ml) and stirred for at least 1 hour. The aqueous phase is extracted three times with 51 ml of ethylacetate. The combined organic phases are washed with water, saturated sodium chloride solution (brine) and dried over magnesiumsulfate. The solvent is evaporated under vacuum. The product may be recrystallized from n-heptane. As the title compound is yielded in highly pure form the recrystallization is not necessary. The title compound may be used directly to start the next step.

The same reaction described above may be carried out with other compounds according to formula IV

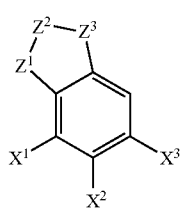

(IV)

wherein $X^1, X^2, X^3, Z^1, Z^2, Z^3$ have the meaning according to the following table:

| | $Z^1$ | $Z^2$ | $Z^3$ | $X^1$ | $X^2$ | $X^3$ |
|---|---|---|---|---|---|---|
| A | O | | | F | | |
| B | | O | | | F | |
| C | | | O | | | F |
| D | NH | | | F | | |
| E | | | O | | F | |
| F | S | | | | | F |
| G | | NH | | Cl | | |

|   | Z¹ | Z² | Z³ | X¹ | X² | X³ |
|---|---|---|---|---|---|---|
| H |   |   | NH |   | Cl |   |
| I |   |   | S |   |   | Cl |
| J |   | S |   | CF₃ |   |   |
| K | S |   |   |   | CF₃ |   |
| L | O |   |   |   |   | CF₃ |
| M |   | O |   | O—CH₃ |   |   |
| N |   |   | O |   | O—CH₃ |   |
| O |   | O | O |   |   | O—CH₃ |
| P | O |   |   |   | F |   |
| Q | NH |   |   |   |   | F |
| R |   | NH |   | NH₂ |   |   |
| S |   |   | NH |   | NH₂ |   |
| T |   |   | O |   |   | Br |

4) Synthesis of [4-(5-fluoro-2,3-dihydrobenzo-furan-7-yl)-4-methyl-2-(trifluoromethyl)pentane-1,2-diol]

A solution of 6.6 mol 4-(5-fluoro-2,3-dihydro-benzofuran-7-yl)-2-hydroxy-4-methyl-2-(trifluoromethyl)pentanoic acid in 77 ml of THF is cooled to 4° C. 12 mmol of lithium aluminumhydride is added portionwise to the solution. The mixture is stirred at 4° C. for 60 minutes, and stirred for 8-9 hours under reflux conditions. After complete reaction (TLC control) the mixture is cooled to 4° C. and treated with 1 ml of saturated NaHCO₃ solution. The mixture is stirred for at least 2 hours whereupon the colour of the mixture turns from grey to white. The precipitated aluminium salts are filtered off and washed with 10 ml of hot THF. The solvent is evaporated under vacuum. The residue is purified by recrystallization from dichloromethane and n-heptane. (yield 73.7%).

Using the compounds according to the table in example 3 further derivatives may be produced in comparable yields.

Starting the reaction sequence with R— or S-2-hydroxy-4-methyl-2-(trifluoromethyl)pentenoic acid in combination with the compounds of general formula IV as described above the following compounds according to formula I may be produced in enantiomerically pure form:

|   | Z¹ | Z² | Z³ | X¹ | X² | X³ | enantiomer |
|---|---|---|---|---|---|---|---|
| a) | O |   |   | F |   |   | R |
| b) |   | O |   |   | F |   | R |
| c) |   |   | O |   |   | F | R |
| d) | NH |   |   | F |   |   | R |
| e) |   | O |   |   | F |   | R |
| f) | S |   |   |   |   | F | R |
| g) |   | NH |   | Cl |   |   | R |
| h) |   |   | NH |   | Cl |   | R |
| i) |   |   | S |   |   | Cl | R |
| j) |   | S |   | CF₃ |   |   | R |
| k) | S |   |   |   | CF₃ |   | R |
| l) | O |   |   |   |   | CF₃ | R |
| m) |   | O |   | O—CH₃ |   |   | R |
| n) |   |   | O |   | O—CH₃ |   | R |
| o) |   | O | O |   |   | O—CH₃ | R |
| p) | O |   |   |   | F |   | R |
| q) | NH |   |   |   |   | F | R |
| r) |   | NH |   | NH₂ |   |   | R |
| s) |   |   | NH |   | NH₂ |   | R |
| t) |   |   | O |   |   | Br | R |
| u) | O |   |   | F |   |   | S |
| v) |   | O |   |   | F |   | S |
| w) |   |   | O |   |   | F | S |
| x) | NH |   |   | F |   |   | S |
| y) |   | O |   |   | F |   | S |
| z) | S |   |   |   |   | F | S |
| aa) |   | NH |   | Cl |   |   | S |
| bb) |   |   | NH |   | Cl |   | S |
| cc) |   |   | S |   |   | Cl | S |
| dd) |   | S |   | CF₃ |   |   | S |
| ee) | S |   |   |   | CF₃ |   | S |
| ff) | O |   |   |   |   | CF₃ | S |
| gg) |   | O |   | O—CH₃ |   |   | S |
| hh) |   |   | O |   | O—CH₃ |   | S |
| ii) |   | O | O |   |   | O—CH₃ | S |
| jj) | O |   |   |   | F |   | S |
| kk) | NH |   |   |   |   | F | S |
| ll) |   | NH |   | NH₂ |   |   | S |
| mm) |   |   | NH |   | NH₂ |   | S |
| nn) |   |   | O |   |   | Br | S |

5) Synthesis of 1,1,1 trifluoro-4-(5-fluoro-2,3-dihydrobenzofuran-7-yl)-4-methyl-2-{[(2-methyl-5-quinoline-5-ylimino]methyl}pentane-2-ol)

To a solution of 3.84 g 4-(fluoro-2,3-dihydrobenzo-furan-7-yl)-4-methyl-2-(trifluoromethyl)pentanal] in 7 ml of acetic acid is added 2.28 g of 5-amino-2-methyl-quinoline at 25° C. 50 ml of toluene is added to the solution and refluxed under Dean-Stark trap for at least 12 hours. After complete reaction (TLC control) the solvent is evaporated under vacuum. Acetic acid is removed by aceotropic destination with toluene. The evaporation residue (Yield 88.7%) is dissolved in alcohol and further processed.

The reaction may be carried out under similar conditions with the amines listed below with comparable results:
1-amino-2-methyl-benzene
1-amino-4-methyl-benzene
2-amino-4-methylpyridine
2-amino-pyridine
2-amino-pyrimidine
3-amino-quinoline
4-amino-pyridine
4-amino-pyrimidine
5-amino-isoquinoline
5-amino-1-methyl-isoquinoline
5-amino-2,6-di-methylquinoline
5-amino-2-methyl-indole
5-amino-2-methyl-isoquinol-1(2H)-one
5-amino-2-methylquinoline
5-amino-6-chloro-2-methylquinoline
5-amino-6-fluoro-2-methylquinoline
5-amino-isoquinol-2(1H)-one
5-amino-quinoline
amino-benzene
N-(4-aminophenyl)-piperidine

6) Synthesis of 1,1,1 trifluoro-4-(5-fluoro-2,3-dihydrobenzofuran-7-yl)-4-methyl-2-{[(2-methyl-5-quinolinyl]methyl}pentane-2-ol)

10 mmol 1,1,1 trifluoro-4-(5-fluoro-2,3-dihydrobenzofuran-7-yl)-4-methyl-2-{[(2-methyl-5-quinoline-5-ylimino]methyl}pentane-2-ol) are dissolved in 255 ml of ethanol. To this solution 5 mmol of sodium bicarbonate is added. The mixture is stirred at 25° C. for 20 minutes. 34 mmol of sodium boronhydride are added to this solution during 10 minutes maintaining the temperature at 0-10° C. The mixture is stirred for 6 hours and another 34 mmol portion of sodium borohydride is added to the solution over 10 minutes maintaining the temperature at 25° C. Then the mixture is stirred at room temperature for 6 hours (TLC control). After completion saturated sodium bicarbonate solution is added over 10 minutes keeping the temperature at 25° C. The mixture is stirred for 60 minutes, and finally the solvent is evaporated under vacuum. The residue is diluted with water and extracted two times with 150 ml of ethyl acetate each. The solvent is evaporated and the residue obtained is purified by recrystallization from ethanol (yield 71.2%).

Using other amines in the reaction of example 5 (e.g. those listen in example 5) and using the other compounds of formula I (e.g. those listed in the table in example 3) quite a number of compounds of general formula VIII may be generated using the methods described herein.

According to the examples described above, it is possible to synthesize the compound according to general formula VIII in 6 steps, whereas the prior art methods needed 13 steps.

The overall yield of the present 6 steps synthesis of compounds of general formula VIII is 14.3% whereas it is 8.7% using the prior art methods.

Moreover, the whole synthetic route can be carried out in enantiomerically pure form, i.e. generating only the desired enantiomer of general formula VIII. This is possible in using chiral 2-hydroxy-4-methyl-2-(trifluoromethyl)pentenoic acid.

It is important to understand that the total yield using chiral 2-hydroxy-4-methyl-2-(trifluoromethyl)pentenoic acid remains approximately 14% whereas it drops to less than 5% according to prior art methods due to the necessary separation of the enantiomers of compound VIII.

The reaction conditions according to the described steps are moreover suitable for production at industrial scale. Excess compounds (e.g. compound IV) can be re-isolated and recycled.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. EP 07090075.8 filed Apr. 18, 2007, European application No. EP 07008931.3 filed May 9, 2007, and U.S. Provisional Application Ser. No. 60/912,596 filed Apr. 18, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A process comprising reducing a compound of formula II

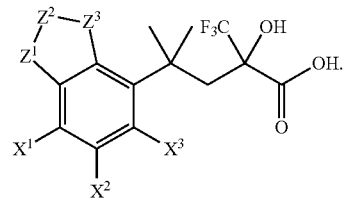

in which at least one of the groups $X^1$, $X^2$, $X^3$ is fluoro, chloro, bromo, hydroxy, methoxy, ethoxy, trifluoromethyl or amino and the other groups $X^1$, $X^2$, $X^3$ are hydrogen,
and in which at least one of the rows $Z^1$, $Z^2$, $Z^3$ is —O—, —S—, —NH— or —N(—CH$^3$)— and the other groups $Z^1$, $Z^2$, $Z^3$ are a —CH$_2$— group,
to obtain an enantiomerically pure compound according to formula I

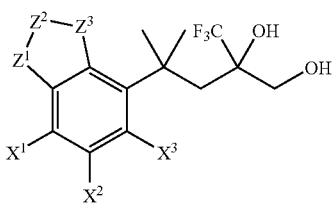

(I)

in which at least one of the groups $X^1$, $X^2$, $X^3$ is fluoro, chloro, bromo, hydroxy, methoxy, ethoxy, trifluoromethyl or amino and the other groups $X^1$, $X^2$, $X^3$ are hydrogen, and in which at least one of the groups $Z^1$, $Z^2$, $Z^3$ is —O—, —S—, —NH—, or —N(—CH$_3$)—, and the other groups $Z^1$, $Z^2$, $Z^3$ are a —CH$_2$— group, wherein said compound of formula II is obtained by reacting a compound according to formula IV

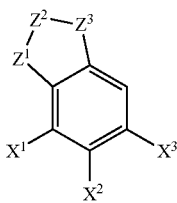

(IV)

in which $X^1$, $X^2$, $X^3$, $Z^1$, $Z^2$, $Z^3$ have the above described meanings with enantiomerically pure 2-hydroxy-4-methyl-2-(trifluormethyl)pentenoic acid

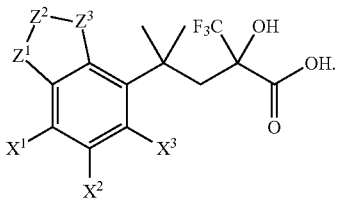

2. A process according to claim 1 in which the reaction of the compound according to formula IV with enantiomerically pure 2-hydroxy -4-methyl-2-(trifluormethyl)pentenoic acid is carried out in a polar solvent in the presence of AlCl3.

3. A process according to claim 2 in which the compound according to formula IV is disolved in a halogenated solvent, AlCl$_3$ is added and the enantiomerically pure 2-hydroxy-4-methyl-2-(trifluormethyl)pentenoic acid is added to the stirred solution.

4. A process according to claim 3 in which the compound according to formula IV is disolved in dichloromethane, AlCl$_3$ is added at 0-5° C. and the enantiomerically pure 2-hydroxy-4-methyl-2-(trifluormethyl)pentenoic acid is added to the stirred solution and stirring continues for 4-120 hours at room temperature.

5. A process according to claim 4 in which approximately 1.5 Eq. of the compound according to formula IV is disolved in dichloromethane, approximately 2 Eq.AlCl$_3$ is added at 0-5° C. and approximately 1.0 Eq. of the enantiomerically pure 2-hydroxy-4-methyl-2-(trifluormethyl)pentenoic acid is added to the stirred solution and stirring continues for 4-120 hours days at room temperature.

6. A process according to claim 1 in which the compound of formula IV has the following substitution pattern:

|   | $Z^1$ | $Z^2$ | $Z^3$ | $X^1$ | $X^2$ | $X^3$ |
|---|---|---|---|---|---|---|
| A | O |   |   | F |   |   |
| B |   | O |   |   | F |   |
| C |   |   | O |   |   | F |
| D | NH |   |   | F |   |   |
| E |   | O |   |   | F |   |
| F | S |   |   |   |   | F |
| G |   | NH |   | Cl |   |   |
| H |   |   | NH |   | Cl |   |
| I |   | S |   |   |   | Cl |
| J |   | S |   | CF$_3$ |   |   |
| K | S |   |   |   | CF$_3$ |   |
| L | O |   |   |   |   | CF$_3$ |
| M |   | O |   |   | O—CH$_3$ |   |
| N |   |   | O |   | O—CH$_3$ |   |
| O |   | O | O |   |   | O—CH$_3$ |
| P | O |   |   |   | F |   |
| Q | NH |   |   |   |   | F |
| R |   | NH |   | NH$_2$ |   |   |
| S |   |   | NH |   | NH$_2$ |   |
| T |   |   | O |   |   | Br. |

7. A process according to claim 1 further comprising oxidizing said enantiomerically pure compound according to formula I

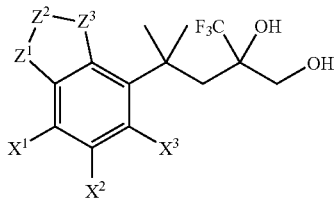

(I)

in which at least one of the groups $X^1$, $X^2$, $X^3$ is fluoro, chloro, bromo, hydroxy, methoxy, ethoxy, trifluoromethyl or amino and the other groups $X^1$, $X^2$, $X^3$ are hydrogen, and in which at least one of the groups $Z^1$, $Z^2$, $Z^3$ is —O—, —S—, —NH—, or —N(—CH$_3$)—, and the other groups $Z^1$, $Z^2$, $Z^3$ are —CH$_2$— to form the enantiomerically pure aldehyde of formula V

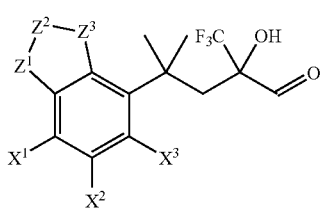

(V)

in which $X^1$, $X^2$, $X^3$, $Z^1$, $Z^2$, $Z^3$ have the above described meanings which is then reacted with an aromatic amine of formula VI H$_2$N—Ar   (VI)

in which Ar is an aromatic group to form an enantiomerically pure imine of formula VII

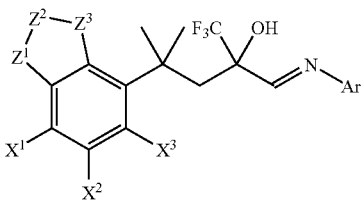

(VII)

in which
at least one of the groups $X^1$, $X^2$, $X^3$ is fluoro, chloro, bromo, hydroxy, methoxy, ethoxy, trifluoromethyl or amino and the other groups $X^1$, $X^2$, $X^3$ are hydrogen, and in which at least one of the groups $Z^1$, $Z^2$, $Z^3$ is —O—, —S—, —NH— or —N(—CH$_3$)—, and the other groups $Z^1$, $Z^2$, $Z^3$ are —CH$_2$— groups
and in which Ar stands for an aromatic group,
which is subsequently reduced to form the compound according to formula VIII

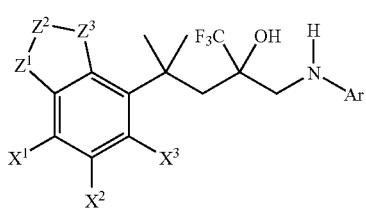

(VIII)

in which at least one of the groups $X^1$, $X^2$, $X^3$ is fluoro, chloro, bromo, hydroxy, methoxy, ethoxy, trifluoromethyl or amino
and the other groups $X^1$, $X^2$, $X^3$ are hydrogen,
and in which at least one of the groups $Z^1$, Z2, $Z^3$ is —O—, —S—, —NH—, or —N(—CH$_3$)—, and the other groups $Z^1$, $Z^2$, $Z^3$ are —CH$_2$— groups
and in which Ar stands for an aromatic group.

8. A process according to claim 7 in which the compound of formula I is reacted with SO3/pyridine complex to form the aldehyde of formula V.

9. A process according to claim 7 in which the compound of formula V is dissolved in acetic acid, the amine of formula VI is added at room temperature, toluene is added and the mixture is refluxed for 5-50 h to yield the imine of formula VII.

10. A process according to claim 7 in which the amine of formula VI is:
1-amino-2-methyl-benzene
1-amino-4-methyl-benzene
2-amino-4-methylpyridine
2-amino-pyridine
2-amino-pyrimidine
3-amino-quinoline
4-amino-pyridine
4-amino-pyrimidine
5-amino-isoquinoline
5-amino-1-methyl-isoquinoline
5-amino-2,6-di-methylquinoline
5-amino-2-methyl-indole
5-amino-2-methyl-isoquinol-1(2H)-one
5-amino-2-methylquinoline
5-amino-6-chloro-2-methylquinoline
5-amino-6-fluoro-2-methylquinoline
5-amino-isoquinol-2(1H)-one
5-amino-quinoline
amino-benzene or
N-(4-aminophenyl)-piperidine.

11. A process according to claim 9 in which the imine of formula VII is reacted with sodium borohydride in alcoholic solution to yield the compound according to formula VIII.

12. A process according to claim 9 in which the amine of formula VI is:
1-amino-2-methyl-benzene
1-amino-4-methyl-benzene
2-amino-4-methylpyridine
2-amino-pyridine
2-amino-pyrimidine
3-amino-quinoline
4-amino-pyridine
4-amino-pyrimidine
5-amino-isoquinoline
5-amino-1-methyl-isoquinoline
5-amino-2,6-di-methylquinoline
5-amino-2-methyl-indole
5-amino-2-methyl-isoquinol-1(2H)-one
5-amino-2-methylquinoline
5-amino-6-chloro-2-methylquinoline
5-amino-6-fluoro-2-methylquinoline
5-amino-isoquinol-2(1H)-one
5-amino-quinoline
amino-benzene
or
N—(4-aminophenyl)-piperidine.

13. A process according to claim 1, wherein said enantiomerically pure 2-hydroxy-4-methyl-2-(trifluormethyl)pentenoic acid is generated via enzymatic hydrolysis of a racemate of alkyl-2-hydroxy-4-methyl-2-(trifluormethyl) pentenoate.

14. A process according to claim 13, in which the enzymatic hydrolysis is carried out in a water solution.

15. A process according to claim 13, in which the enzyme is:
*Candida cylindracea* Lipase C1, *Candida cylindracea* Lipase C2, *Achromobacter sp* Lipase A, *Alcaligenes sp* Lipase AS1, *Aspergillus niger* Lipase AN, *Penicillium cambertii* Lipase PC, *Pseudomonas fluorescens* Lipase PF, *Candida antarctica* Lipase B (CALB), *Pseudomonas fluorescens* Lipase AH, *Pseudomonas fluorescens* Lipase AK, *Candida rugosa* Lipase AYS, *Pseudomonas stutzeri* Lipase PS, *Aspergillus melleus* Protease K, *Bacillus subtilis* Protease N, *Aspergillus melleus* Protease P, *Aspergillus sp.* Lipase (ICR-101), *Rhizopus sp.* Lipase (ICR-102), *Rhizopus oryzae* Lipase (ICR-103), *Penicillium sp.* I Lipase (ICR-104), *Penicillium sp.* II Lipase (ICR-105), *Candida rugosa* Lipase (ICR-106), *Pseudomonas cepacia* Lipase (ICR-107), *Pseudomonas sp.* Lipase (ICR-108), *Pseudomonas fluorescens* Lipase (ICR-109), *Candida antarctica* Lipase (ICR-110), *Candida sp.* Lipase (ICR-111), *Candida antarctica* Lipase (ICR-112), *Pseudomonas sp.* Lipase (ICR-113), Porcine pancreas Lipase (ICR-114), *Thermomyces lanuginosus* Lipase (ICR-115), *Mucor miehei* Lipase (ICR-116), *Alcalicenes sp.* Lipase (ICR-117), *Streptomyces griseus* protease (ICR-118), *Bacillus lentus* & *Bacillus licheniformis* protease (ICR-119), *Bacillus sp.* protease (ICR-120) *Candida antarctica* Lipase typ B, carrier fixed (IMB-102) *Rhizomucor miehei* Lipase, carrier fixed (IMB-105), *Bacillus sp.* Esterase BS1, *Bacillus sp.* Esterase BS2, *Bacillus sp.* Esterase BS3, Esterase PF2, Pork Liver Esterase PL, *Bacillus licheniformis* alpha amylase (DURAMYL), *Candida Antarctica* Cellulase (NOVOZYME 868), *Candida Antarctica* Lipase (NOVOZYME 525L), *Rhizomucor miehei* Lipase (NOVOZYME 388), *Bacillus amyloliquefaciens* Protease (NEUTRASE 0), Lipase (LIOPOASE), Lipase from porcine pancreas Typ II, Esterase from porcine liver or Lipase from *Candida rugosa*.

16. A process according to claim 14, in which the enzyme is: *Candida cylindracea* Lipase C1, *Candida cylindracea* Lipase C2, *Achromobacter sp* Lipase A, *Alcaligenes sp* Lipase AS1, *Aspergillus niger* Lipase AN, *Penicillium cambertii* Lipase PC, *Pseudomonas fluorescens* Lipase PF, *Candida antarctica* Lipase B (CALB), *Pseudomonas fluorescens* Lipase AH, *Pseudomonas fluorescens* Lipase AK, *Candida rugosa* Lipase AYS, *Pseudomonas stutzeri* Lipase PS, *Aspergillus melleus* Protease K, *Bacillus subtilis* Protease N, *Aspergillus melleus* Protease P, *Aspergillus sp.* Lipase (ICR-101), *Rhizopus sp.* Lipase (ICR-102), *Rhizopus oryzae* Lipase (ICR-103), *Penicillium sp.* I Lipase (ICR-104), *Penicillium sp.* II Lipase (ICR-105), *Candida rugosa* Lipase (ICR-106), *Pseudomonas cepacia* Lipase (ICR-107), *Pseudomonas sp.* Lipase (ICR-108), *Pseudomonas fluorescens* Lipase (ICR-109), *Candida antarctica* Lipase (ICR-110), *Candida sp.* Lipase (ICR-111), *Candida antarctica* Lipase (ICR-112), *Pseudomonas sp.* Lipase (ICR-113), Porcine pancreas Lipase (ICR-114), *Thermomyces lanuginosus* Lipase (ICR-115), *Mucor miehei* Lipase (ICR-116), *Alcalicenes sp.* Lipase (ICR-117), *Streptomyces griseus* protease (ICR-118), *Bacillus lentus* & *Bacillus licheniformis* protease (ICR-119), *Bacillus sp.* protease (ICR-120) *Candida antarctica* Lipase typ B, carrier fixed (IMB-102) *Rhizomucor miehei* Lipase, carrier fixed (IMB-105), *Bacillus sp.* Esterase BS1, *Bacillus sp.* Esterase BS2, *Bacillus sp.* Esterase BS3, Esterase PF2, Pork Liver Esterase PL, *Bacillus licheniformis* alpha amylase (DURAMYL), *Candida Antarctica* Cellulase (NOVOZYME 868), *Candida Antarctica* Lipase (NOVOZYME 525L), *Rhizomucor miehei* Lipase (NOVOZYME 388), *Bacillus amyloliquefaciens* Protease (NEUTRASE 0), Lipase (LIOPOASE), Lipase from porcine pancreas Typ II, Esterase from porcine liver or Lipase from *Candida rugosa*.

17. A process according to claim 15, wherein said enzyme is *Aspergillus melleus* Protease K.

* * * * *